US006485943B2

(12) United States Patent
Stevens et al.

(10) Patent No.: US 6,485,943 B2
(45) Date of Patent: *Nov. 26, 2002

(54) METHOD FOR ALTERING ANTIBODY LIGHT CHAIN INTERACTIONS

(75) Inventors: Fred J. Stevens, Naperville, IL (US); Priscilla Wilkins Stevens, Evanston, IL (US); Rosemarie Raffen, Elmhurst, IL (US); Marianne Schiffer, Downers Grove, IL (US)

(73) Assignee: The University of Chicago, Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/274,163

(22) Filed: Mar. 22, 1999

(65) Prior Publication Data

US 2002/0137897 A1 Sep. 26, 2002

Related U.S. Application Data

(62) Division of application No. 08/373,380, filed on Jan. 17, 1995, now abandoned.

(51) Int. Cl.⁷ .............................................. C12N 15/00
(52) U.S. Cl. .................... 435/69.6; 530/387.1; 530/350
(58) Field of Search ...................... 435/69.6; 530/387.3, 530/350, 387.1; 536/23.1, 23.53

(56) References Cited

PUBLICATIONS

Raffen et al., Protein Engineering 11:303–309, 1998.*
Chan et al., Folding and Design 1:77–89, 1996.*
Steipe, B. et al. J. Mol. Biol. 225: 739–753, 1992.
Freund, C. et al. Biochemistry 33: 3296–3303, 1994.
Pluckthun, A. et al. Bio/Technology 9: 545–551, Jun. 1991.
Ward, E.S. et al. FASEB Journal 6: 2422–2427, Apr. 1992.
Cheadle, C. et al. Mol. Immunol. 29: 21–30, Jan. 1992.
Buchner, J. et al. Bio/Technology 9: 157–162, Feb. 1991.
Fred J. Stevens, et al., "Self–Association of Human Immunoglobulin κI Light Chains: Role of the Third Hypervariable Region," *Proc. Natl. Acad. Sci. USA*, vol. 77, No. 2, Feb. 1980, pp. 1144–1148.

Chong–Hwan Chang, et al., "Novel Arrangement of Immunoglobulin Variable Domains: X–Ray Crystallographic Analysis of the λ–Chain Dimer Bence–Jones Protein Loc," *Biochemistry*, vol. 24, No. 18, 1985, pp. 4890–4897.

Fred J. Stevens, et al., "Dual Conformations of an Immunoglobulin Light–Chain Dimer: Heterogeneity of Antigen Specificity and Idiotope Profile May Result from Multiple Variable–Domain Interaction Mechanisms," *Proc. Natl. Acad. Sci. USA*, vol. 85, Sep. 1988, pp. 6895–6899.

M. Schiffer, et al., "Structure of a Second Crystal Form of Bence–Jones Protein Loc: Strikingly Different Domain Associations in Two Crystal Forms of a Single Protein," *Biochemistry*, vol. 28, No. 9, 1989, pp. 4066–4072.

Arne Skerra, Bacterial Expression of Immunoglobulin Fragments, *Immunology*, vol. 5, 1993, pp. 256–262.

Fred J. Stevens, "Analysis of Protein–Protein Interaction by Simluation of Small–Zone Size Exclusion Chromatography," *Biophysical Journal*, vol. 55, Jun. 1989, pp. 1155–1167.

Fred J. Stevens, et al., "Computer Simulation of Protein Self–Association During Small–Zone Gel Filtration," *Biochem. J.*, vol. 195, 1981, pp. 213–219.

* cited by examiner

*Primary Examiner*—Sheela Huff
*Assistant Examiner*—Larry R. Helms
(74) *Attorney, Agent, or Firm*—Foley & Lardner

(57) ABSTRACT

A method for recombinant antibody subunit dimerization including modifying at least one codon of a nucleic acid sequence to replace an amino acid occurring naturally in the antibody with a charged amino acid at a position in the interface segment of the light polypeptide variable region, the charged amino acid having a first polarity; and modifying at least one codon of the nucleic acid sequence to replace an amino acid occurring naturally in the antibody with a charged amino acid at a position in an interface segment of the heavy polypeptide variable region corresponding to a position in the light polypeptide variable region, the charged amino acid having a second polarity opposite the first polarity. Nucleic acid sequences which code for novel light chain proteins, the latter of which are used in conjunction with the inventive method, are also provided.

19 Claims, 8 Drawing Sheets

```
        01_          11_          21_          27D          35_          45_
len  : DIVMTQSPDS   LAVSLGERAT   INCKSSQSVL   YSSNSKNYLA   WYQQKPGQPP   KLLIYWASTR
lenR:                                                       R
lenK:                                                       K
lenD:                                                       D 55_          65_          75_          85_          95_          99_
len  : ESGVPDRFSG   SGSGTDFTLT   ISSLQAEDVA   VYYCQQYYST   P......YSF   GQGTKLEI.K
lenR:
lenK:
lenD:
```

FIG. 8

METHOD FOR ALTERING ANTIBODY LIGHT CHAIN INTERACTIONS

This application is a divisional of application Ser. No. 08/373,380, now abandoned, filed Jan. 17, 1995.

The United States Government has rights in this invention pursuant to Contract No. W-31-109-ENG-38 between the U.S. Departrnent of Energy (DOE) and the University of,Chicago representing Argonne National Laboratory.

BACKGROUND OF THE INVENTION

The present invention relates generally to methods for optimizing production of recombinant antibodies and nucleic acid sequences which code for novel light chain proteins, the later of which are used in conjunction with the inventive methods. More particularly, the novel light chains which demonstrate the efficacy of the inventive methods can also be utilized in conjunction with a panel for comparing the amino acid sequences of amyloid-associated unmunoglobulin light chains to sequences of non-pathogenic light chains. In such a manner protein regions responsible for self-association and fibril formation can be identified and, ultimately, provided a basis for rational drug design.

Detailed analyses of the structures and biophysical properties of unmunoglobulin molecules have, over the years, probed many aspects of immunoglobulin function, particularly antibody-antigen interactions and effector functions. See Padlan,*Anatomy of the Antibody Molecule,* Mol. Immunol. 31:169–217, 1994. Immunoglobulin genes have been cloned and altered by mutagenesis to investigate effects of the changes on biological activities, and synthetic immunoglobulin genes have been generated for the production of unique antibody reagents for medical and diagnostic purposes. Another important area of immunoglobulin biology and analysis is the structural characterization of pathological protein deposits formed in humans when plasma cell dyscrasias result in excess production of immunoglobulin protein chains.

Amyloidosis is a severe pathological condition in which deposits of extracellular protein form insoluble fibers in tissues. Amyloid fibers are non-branching fibrils of diameter 70–100 A. Birefringence of bound Congo Red dye demonstrates that proteins within an amyloid fibril are highly ordered. The fibrils are virtually insoluble, except under extremely denaturing conditions, suggesting a large number of molecular interactions contribute to amyloid stability. These tissue deposits impair organ function, and extensive amyloid deposition can lead to death due to organ failure. Many different types of proteins are known to form amyloids, but any particular amyloid deposit contains an essentially homogeneous protein core of primarily β-sheet structure. See Stone, *Amyloidosis: A Final Common Pathway for Protein Deposition in Tissues,* Blood 75:531–545, 1990. In light chain amyloidosis (AL-amyloidosis) a monoclonal immunoglobulin light chain forms the amyloid deposits. See Glenner et al., *Amyloid Fibril Proteins: Proof of Homology with Immunoglobulin Light Chains by Sequence Analyses,* Science 172:1150–1151, 1971. Amyloid fibrils from patients suffering AL-amyloidosis occasionally contain only intact light chains, but more often they are formed by proteolytic fragments of the light chains which contain the VL domain and varying amounts of the constant domain, or by a mixture of fragments and fuil-length light chains. Not all light chains from plasma cell dyscrasias form protein deposits; some circulate throughout the body at high concentrations and are excreted with the patients urine without pathological deposition of the protein in vivo. See Solomon, *Clinical Implications of Monoclonal Light Chains,* Semin. Oncol. 13:341–349, 1986; Buxbaum, *Mechanisms of Disease: Monoclonal Immunoglobulin Deposition, Amyloidosis, Light Chain Deposition Disease, and Light and leavy Chain Deposition Disease,* Hematol/Oncol. Clinics of North America 6:323–346, 1992; and Eulitz, *Amyloid Formation from Immunoglobulin Chains,* Biol. ChenL Hoppe-Seyler 373:629–633, 1992.

In some types of hereditary amyloidoses, single amino acid changes in normal human proteins are responsible for amyloid fibril fornation See Natvig et al., *Amvloid and Amyloidosis* 1990. Dordrecht, The Netherlands: Kluwer Academic Publishers, 1991, and references cited therein. It is unlikely, however, that any single amino acid position or substitution will fully explain the many different immunoglobulin light chain sequences associated with AL-amyloidosis. Rather, several different regions of the light chain molecule may sustain one or more substitutions which affect a number of biophysical characteristics, such as dimer formation, exposure of hydrophobic residues, solubility, and stability.

Increased dimerization, for example, may promote amyloid deposition of a protein. It has been shown that an extremely high proportion of rREC occurs as dimers, even at very low concentrations of the recombinant protein. The calculated dimerization constant for rREC is ~$10^7$, approximately two orders of magnitude higher than that of rLEN. The dimerization constant of rLEN, ~$5 \times 10^5$ $M^{-1}$, is in the range of self-association constants observed for other human immunoglobulin light chains. For KI protein AU, for example, a value of $6.6 \times 10^4$ $M^{-1}$ was experimentally determined (see Maeda et al.,Kinetics of Dimerization of the Bence-Jones Protein AU,Biophys. Chem. 9:57–64, 1978); values from ~$10^3$ $M^{-1}$ to ~$10^6$ $M^{-1}$ were estimated for a large number of human immunoglobulin KI light chains (see Stevens et al., *Self-association of Human Immunoglobulin κI Light Chains: Role of the Third Hypervariable Region,* Proc. Natl. Acad. Sci. USA 77:1144–1148, 1980); and values of ~$2.5 \times 10^5$ $M^{-1}$ to ~$5.0 \times 10^6$ $M^{-1}$ were calculated for variant REI VKI domains. Computer simulation of rREC dimerization, however, yield a dimerization constant of $5 \times 10^7$ $M^{-1}$.

It has been suggested that unusual amino acids within the inner β-sheets which form the contact regions at the dimer interface may be responsible for increasing dimer stability of amyloidogenic light chains, thereby promoting fibril formation. See Dwulet et al., *Amino Acid Sequence of a ⊖ VI Primary (AL) Amyloid Protein.* Scand. J. Immunol. 22:653–660, 1985; Liepnicks et al., *Comparison of the Amino Acid Sequences of ten kappa I Amyloid Proteins for Amyloidogenic Sequences,* In: Natvig J B, et al. Amyloid and Amyloidosis 1990. Dordrecht, The Netherlands: Kluwer Academic Publishers, pp. 153—156, 1991; and Aucouturier et al., *Complementary DNA Sequence of Human Amyloidogenic Immunoglobulin Light-Chain Precursors.* Biochem. J. 285:149–152, 1992. The positional effect of amino acids is illustrated by two unanticipated features in the crystallographic structures of naturally occuhing light chains obtained from human patients. In one structural investigation study, a glutamine residue at position 38 was observed to have been replaced by a histidine residue in the Bence-Jones protein Loc. The crystal structure of the protein crysted from ammonium sulfate differed from that of the protein crystallized from distilled water. The quaternary interactions exhibited by the protein in the two crystal forms were sufficiently different to suggest fimdalmentally different interpretations of the structural basis for the function of this protein. See Schiffer et al, *The Structure of a Second Crystal Form of Bence Jones Protein Loc: Strikingly Different Domain Associations in Two Crystal Forms of a Single Protein*, Biochemistry 28:4066–4072, 1989. In a second crystallographic analysis, a highly conserved tyrosine residue at position 36 was observed to have been replaced by a phenylalanine residue, the structural differences again suggesting an altered quaternary interaction. See Huang et al., *Novel Immunoglobulin Variable Domain Interaction is Observed*, American Crystallographic Association Meeting, 1993, p 127. Notwithstanding findings of this sort, the stability of amyloidogenic dimers is not fully understood: The sequence of the amyloid protein REC differs from that of LEN primarily at CDR residues and not at residues comprising the β-sheet framework.

Nonetheless, there has been great interest in deteimining the sequences of amyloid-associated immunoglobulin light chains and comparing them to sequences of non-pathogenic light chains to identify regions of the proteins responsible for self-association and fibril formation. A substantial number of sequences of amyloidogenic immunoglobin in light chains have been obtained either by direct amino acid sequencing of protein isolated from patient urine or from amyloid deposits or by nucleotide sequencing of cDNAs cloned from plasma cells of patients with AL-type amyloidosis, but no particular common sequences have been identified as obviously correlating with the pathogenic properties of the amyloid-associated light chains. See Natvig et al., supra; Aucouturier et al., supra, and references cited therein.

Another approach to understanding the molecular differences between non-pathogenic and amyloidogenic light chais is to probe the in vivo disease process of protein deposition by in vitro exammation of various biochemical and biophysical properties of light chain proteins which either are "benign" or form protein deposits in vivo. See Solomon, *Bence Jones Proteins: Malignant or Benign? N. Engl. J. Med.* 306:605–607, 1982; and Myatt et al., *Pathogenic Potential of Human Monoclonal Immunoglobulin Light Chains: Relationship of in vitro Aggregation to in vivo Organ Deposition*, Proc. And. Acad. Sci. USA 91:3034–3038, 1994. Characterization of the chemical anctphysical properties of amyloid-associated immunoglobulii light chains has been difficult, however. Because these light chains accumulate in insoluble extracellular deposits, it is generally difficult to obtain the relevant light chain protein from patient serum or urine in quantities sufficient for analyses. Solubilintion of light chain proteins from amyloidladen tissue obtained post mortem requires harsh chemical treatments and provides only a limited, non-replenishable protein supply.

A somewhat effective approach has been to apply recombinant bacterial techniques enroute to both benign immunoglobulin light-chain domains and those known to produce pathological deposits. In such a manner, large quantities of light chain proteins are available, such that their biophysical and biochemical properties can be thoroughly studied. Comparisons of the benign and pathological light chains can provide the basis for production of mutated proteins modified at particular residues for in vitro analysis of the effects of these mutations on various biophysical characteristics.

Traditionally, antibodies have been obtained by the immunization of animals, such as goats and rabbits, and subsequent purification from the animal blood. The quality of the antisera intermittently obtained from a single animal was variable, and the characteristics of the antisera obtained from any two animals were often different. Methods were subsequently developed which allowed the fusion of an antibody-producing lymphocyte with an immortal myeloma cell; i.e., a cancerous lymphocyte capable of continuous replication. Such hybridomas became sources of chemically homogeneous monoclonal antibodies which allowed for more predictable and controllable technological application More recently, techniques were developed for the transfer of antibody genes into bacteria. These recombinant bacteria produce antibodies identical to those produced by the aniimal from which the gene was obtained.

However, recombinant techniques are not without problems and deficiencies. Effective commercial use of recombinant antibodies for immunodiagnostic, immunotherapeutic, or other applications in industrial, environmental and/or agricultural fields requires maiial yields. In many cases, even where synthesized by bacteria, the productivity of functional antibody is erratic and is frequently too low to be useful. Less than optimal productivity is often related to diminished functional Fab and Fv assemblies, resulting from homologous dimer self-association.

OBJECTS OF THE INVENTION

It is, therefore, an object of this invention to provide a method for increased yields of synthesized recombinant antibody, overcoming the problems and deficiencies of the prior art, including those discussed above.

It is also an object of this invention to provide a method for increased yields of synthesized recombinant antibody, utilizing, inter alia, improved control of variables related to antibody assembly.

Another object of this invention is to provide novel light chains which demonstrate the efficacy of the inventive methods.

Another object of this invention is to characterize the molecular interactions involved in amyloid fibril formation, stability, and insolubility enroute to the development of effective therapies.

Another object of this invention is to provide novel light chains or fragments thereof for use in conjunction with a panel for comparing the amino acid sequences of amyloid-associated immunoglobulin light chain sequences of non-pathogenic light chains.

Another object of this invention is to enhance assembly of functional variable domain fragments.

Another object of this iiveiion is to provide a method for light chain and heavy chain variable domain complex formation, such that the complex is capable of binding antigen.

Another object of this invention is to provide a method for antigen binding fragment fotmation.

Another object of this invention is to favorably influence the rate of variable domain fcragent assembly, increasing the concentration of heavy and/or light chain variable domain, suce that the fragment yield is increased.

Another object of this invention is to lower the equilibrium constant for one or both homologous variable domain associations and/or reduce the incidence of such reactions in competition with heterologous dimerizations.

Another object of this invention is to cbncombinantly increase heterologous associations and decrease homologous associations.

Another object of this invention is to increase the yield of recombinant Fv and Fab assemblies through modification of the amino acid sequence in the interfacial segments of the light and heavy chain variable domains.

Another object of this invention is to increase the yield of antigen binding fragment and variable domain fragnent assemblies by altering the free energy requirements of dimerizaton and promoting productive variable domain associations.

Another object of this invention is to alter the amino acid sequence of light and heavy chain variable domains to provide energetically favorable contacts across the variable domain interface.

Another object of this invention is to increase productive associations through modification of variable domain affinity and/or geometry by rational substitution of interfacial amino acids.

Another object of this invention is to apply the principles and/or precepts underline any and each of the foregoing objects to modification of nucleic acid sequences coding for antibody subunits of light and heavy polypeptides and the expression of the modified sequences.

Other objects, features and advantages of the present invention will be readily apparent from the following description of the preferred embodiments thereof, taken in conjunction with the accompanying examples, figures, and sequences.

BRIEF DESCRIPTION OF THE DRAWINGS

FIG. 8, using the IUPAC-IUB Biochemistry Nomenclature, shows, without the nucleic acid sequences, the amino acid sequences for the wild-type Len proteins of this invention (len), SEQ ID NOS: 43–49 and substitutions of arginine (R), lysine (K), and aspartic acid (D)—len R, SEQ ID NOS: 2,4,6,8,10,12 and 14 len K and len D, SEQ ID NOS: 16,18,20,22,24,26 and 28 respectively—for glutamine (Q) at position 38. Amino acid positions are numbered, employing the Wu-Kabat convention. There are no codons for positions 95*a* through 95*f* and 106*a* ( . . . ) which are not occupied by amino acids in kappa-IV light chains, although positions 27*a*–27*f* are coded and are occupied. The proteins of FIG. 8 (SEQ ID NOS: 2, 4 and 6) are specified by the codons of SEQ ID NOS: 43–49, SEQ ID NOS: 30,32,34,36,38,40 and 42, SEQ ID NOS: 2,4,6,8,10, 12 and 14, and SEQ ID NOS: 16,18,20,22,24,26 and 28, respectively.

SUMMARY OF THE INVENTION

Figure 1:
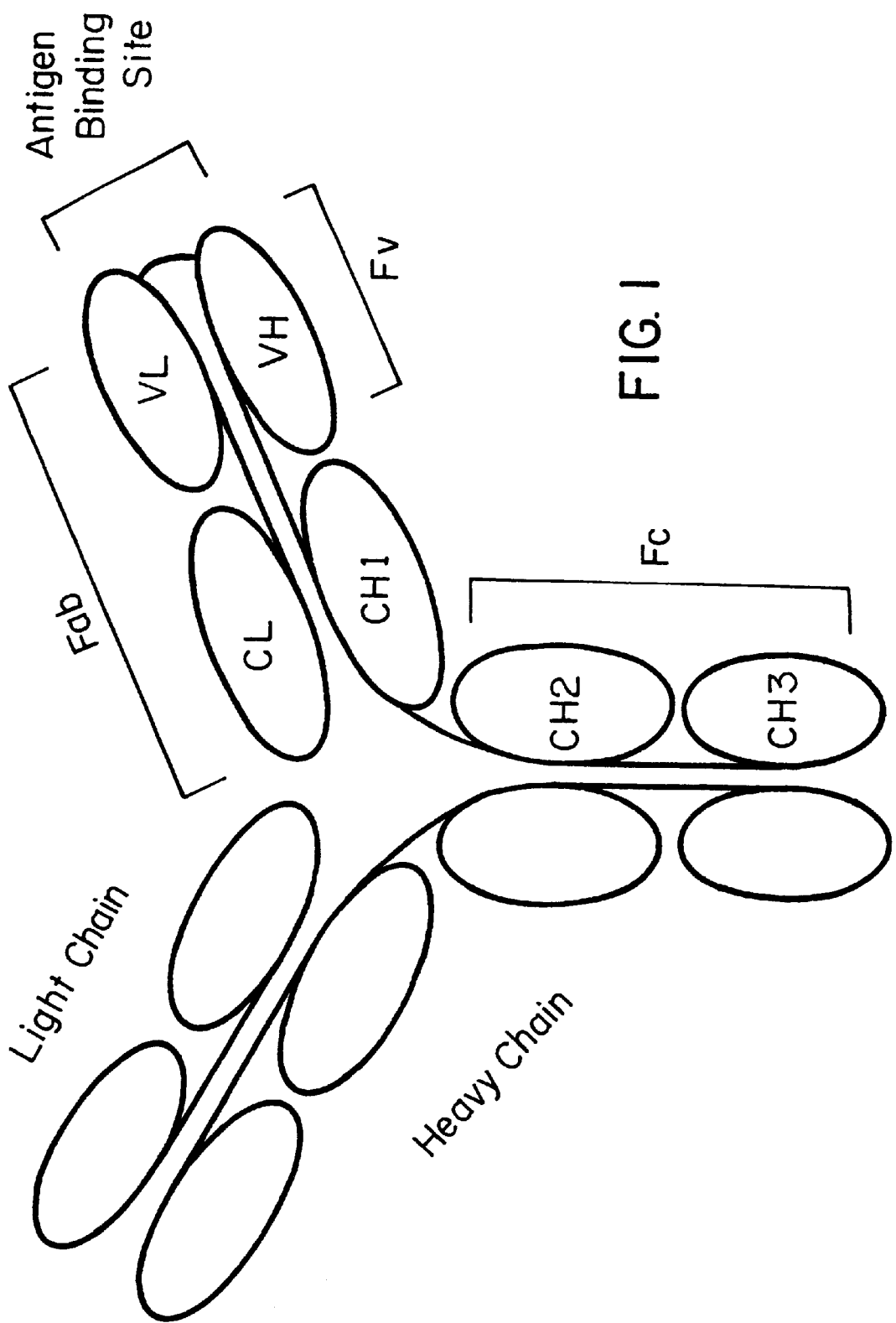
FIG. 1 is a schematic representation of a typical multi-subunit antibody protein having two heavy and two light polypepticle chains. Using one of several conventions well-known to those skilled in the art, Fab represents an antigen binding fragent; Fv—variable domain frament; Fc—crystallizable fragment; VL—light chain variable domain; VH—heavy chain variable domain; CL—light chain constant domain; and CHx—heavy chain constant domains.

This invention entails a method for improved recombinant antibody production and novel light chain proteins which can be used in conjunction therewith. The invention overcomes certain well-known problems and deficiencies, including those outlined above.

In part, the present invention is a method for improved recombinant antibody subunit dimerization, including: (1) providing nucleic acid sequences which code for a plurality of antibody subunits having heavy polypeptides, wherein each of the polypeptide further includes at least one constant region or one variable region with interacting interface segments; (2) modifying at least one codon of nucleic acid sequence to replace an amino acid occuring naturally in the antibody with a charged amino acid at a position in each interface segment of the light polypeptide variable region, such that the charged amino acid has a first polarity; (3) modifying at least one codon of nucleic acid sequence to replace an amino acid occurring naturally in the antibody with a charged amino acid at a position in each interface segment of the heavy polypeptide variable region corresponding to the position in the light polypeptide variable region, such that this charged amino acid has a second polarity opposite the polarity of the first charged amino acid; (4) expressing the modified nucleic acid sequence; and (5) interacting the modified heavy and light polypeptide variable regions of the expressed sequence.

Preferably, the modified nucleic acid sequences are cloned and expressed by bacteria. In preferred embodiments, the modified heavy variable region is expressed in a first recombinant bacteria, and the modified light polypeptide variable region is expressed in a second recombinant bacteria. In highly preferred embodiments, the expressed modified variable regions are assembled into heterologous dimers.

Preferably, the charged amino acids substituted in each variable region, through modification of a nucleic acid sequence, are selected from the group consisting of aspartic acid, lysine, arginine, and glutamic acid. In preferred embodiments, the light polypeptide variable region is modified by replacement of glutamine with aspartic acid in the light polypeptide interface segnent; and the heavy polypeptide variable region is modified by replacement of glutamine with either lysine or arginine in the heavy polypeptide interface segment.

In preferred embodiments, the nucleic acid sequences code for a light polypeptide interacting with a corresponding heavy polypeptide through at least one of positions 36, 38, 87, 89, 96, and 98 of the interface segment of the light polypeptide variable region. Likewise, in preferred embodiments, the light polypeptide is selected from the group consisting of kappa and lambda constructs, and the charged amino acids are selected from the group consisting of asparic acid, lysine, arginine, and glutamic acid. In highly preferred embodiments, the light polypeptide variable region is modified by replacement of glutamine with either aspartic acid or glutamic acid at interfacial position 38, and the heavy polypeptide variable region, and the heavy polypeptide variable region is modified by replacement of either lysine or arginine at the corresponding interfacial position. It will be understood by those skilled in the art and aware of this invention that the standard lambda construct is identical to the standard kappa construct, with respect to the interface framework but for a lysine residue at position 38 and a phenylalanine residue at position 36.

Alternatively, in highly preferred embodiments, the light polypeptide variable region is modified by replacement of glutaine with either lysine or arginine at interfacial position 38, and the heavy polypeptide variable region is modified by replacement with either aspartic acid or glutamic acid at a corresponding interfacial position on the heavy polypeptide variable region. The method for improved recombinant antibody dimerization can further include modifying the nucleic acid sequences to remove hydrophobic amino acids naturally occurring in the antibody from the interface segment of the heavy polypeptide variable region.

In part, the present invention is a method for increasing heterologous immunoglobulin domain affinity, including: (1) providing a light chain having a variable domain, wherein the domain is modified by substitution of at least one interfacial position with a first charged amino acid having a first polarity; (2) providing a heavy chain with a variable domain, wherein the domain is modified by substitution of at least one interfacial position with a second charged amino acid—the heavy chain interfacial position corresponding to the light chain interfacial position—such that the second charged amino acid has a polarity opposite that of the first charged amino acid; and (3) interacting the modified heavy and light chains to induce heterologous dimerization, such that production of functional antigen binding and variable domain fragments is enhanced.

Preferably, the first and second charged amino acids are selected from the group consisting of asparic acid, lysine, arginine, and glutamic acid. In highly preferred embodiments, the light variable chain domain is modified by substiution with either aspartic acid or glutamic acid at the interfacial position; and the heavy variable chain domain is modified by substitution with either lysine or arginine at the interfacial position. Alternatively, light chain variable domain is modified by substitution with either lysine or arginine at the interfacial position; and the heavy chain variable domain is modified by substitution with either aspartic acid or glutamic acid at an interfacial position.

The immunoglobulin of the present invention can be selected from the group consisting of IgG, IgA, IgM, IgD and IgE globulins. In preferred embodiments, the light chain is a kappa IV protein. In highly preferred embodiments, the light chain protein variable domain is modified in at least one of interfacial positions 36, 38, 87, 89, 96, and 98, while the heavy chain protein variable domain is modified at a corresponding subset of interfacial positions. Modification can be achieved through use of the first and second charged amino acids selected from the group consisting of aspartic acid, lysine, arginine, and glutamic acid. Likewise, in highly preferred embodiments, the light chain variable domain is modified by substitution with either aspartic acid or glutamic acid at interfacial position 38, and the heavy chain variable domain is modified by substitution with either lysine or arginine at interfacial position 39. Preferably, the light chain variable domain is modified by aspartic acid substitution, and a heavy chain variable domain is modified by arginine substitution.

In part, this invention is a variant kappa IV light chain protein having an amino acid sequence such as that shown in SEQ ID NO: 2, SEQ ID NO: 4, or SEQ ID NO: 6. Preferably, the amino acid at position 38 under the Wu-Kabat convention is a charged residue and/or is selected from the group consisting of arginine, lysine, and aspartic acid.

In part, the present invention is a nucleic acid sequence comprising a coding region for a protein having an amino acid sequence such as that shown in SEQ ID NO: 2, SEQ ID NO: 4, or SEQ ID NO: 6. The sequence codes for a protein having a charged residue at position 38, preferably one selected from the group consisting of arginine, lysine and aspartic acid. In highly preferred embodiments, the coding region is selected from the group consisting of the codon sequence in SEQ ID NO: 2, the codon sequence of SEQ ID NO: 4; the codon sequence of SEQ ID NO: 6; and nucleic acid sequences complementary to the aforementioned codon sequences. Without limitation and as well-known to those skilled in the art, the later sequences include those complementary to DNA, mRNA, and tRNA. With respect to the kappa-IV light chain proteins of this invention, the degeneracy of the genetic code is contemplated such that position 38 and analogous residues can be specified by more than one codon. The nucleic acid sequences can further include vector DNA, such that the coding region can be introduced into a host cell.

As referenced above and shown schematically in FIG. 1, a typical antibody is a multisubunit protein comprising four polypeptide chains; two "heavy" chains and two "light" chains. An IgG-type antibody has a molecular weight of approximately 150,000 daltons. Each chain or subunit consists of multiple subunits, distinct globular independent modules. The heavy chain has four domains, the light chain has two domains. All of the domains are classified as either variable or constant. As well-known to those skilled in the art, constant refers to the relative similarity of these domains when antibodies from one individual or species are compared, while variable domains are much more heterogeneous in structure—it is this variability that accounts for antibody diversity. Most of the variability is restricted to one region of the domain when it is folded into its functional three-dimensional shape.

The two heavy chains are held together by strong non-covalent CH3—CH3 domain intactions, and one or more disultide bonds between the "switch" peptide segments that connect the CH1 and CH2 domains. The light chain combines with the heavy chain via noncovalent VL-VH and CL-CH1 interactions and a disulfide bond between CL and CH1. The four domain complex consisting of the light chain and the two heavy chain domains is termed the Fab or antigen binding fragment. This fragment was traditionally generated by enzymatic digestion of an intact antibody but can now also be synthesized directly through recombinant DNA technology, as referenced above. The complex of the light chain and heavy chain variable domains is known as the Fv and is also capable of binding antigen. The antigen binding site contains contributions from both the heavy chain and light chain variable domain. Alteration of the amino acid sequence in the portion of the antigen combining site results in altered substrate specificity and affinity. Because the functional properties of the antigen combining site depend upon the relative positions of atoms located in two independent domains, it is clear that alteration of the geometric relationship of the light chain and heavy chain vaiable domains will significantly alter the antigen binding properties of an antibody.

Without restriction to any one theory or interpretation, the method of the present invention can be considered in conjunction with the assembly of a functional Fv component which can be represented by equation (1):

$$VH + VL \rightleftharpoons Fv \qquad (1)$$

where the double arrow represents the bidirectionality of the domain interaction Fv assemblies also dissociate to form free VH and VL domains; at equilibrium the rates of formation and dissociation of Fv are equal. The concentration of Fv is given by equilibrium expression (2) below:

$$[Fv] = K_{HL}[VH][VL] \qquad (2)$$

where the bracketed terms are the molar concentrations of Fv, VH, and VL, respectively, at equilibrium. $K_{HL}$ is the equilibrium constant for this interaction and represents the affinity or "strength" of interaction between the VH and VL domains.

When bacteria are used to synthesize functional Fv assemblies, genes for both VH and VL domains are expressed; i.e., turned on, simultaneously. However, VH and VL domains are capable of homologous association with themselves as well as heterologous association with each other. Therefore, instead of a single productive interaction (equation 1), there are two additional simultaneous, competing reactions (equations 3 and 4).

$$VH + VH \rightleftharpoons HH \qquad (3)$$

$$VH + VL \rightleftharpoons Fv \qquad (1)$$

$$VL + VL \rightleftharpoons LL \qquad (4)$$

where HH and LL indicate dimers of VH and VL, respectively. The relative equilibrium concentrations of Fv, HH, and LL are governed by the three equilibrium constants $K_{HL}$, $K_{HH}$, and $K_{LL}$, respectively. However, an equilibrium condition is not necessarily reached. Dimers of VH form large molecular weight aggregates (HH) and subsequently precipitate (equation 3), rendering VH domains unavailable for interaction with VL to form Fv. As Fv dissociation releases VH, continuous precipitation of HH can occur. If $K_{HH}$ is comparable in magnitude to $K_{HL}$, the result can be vitally complete elimination of Fv formation.

A second competing reaction is the formation of VL dimers (equation 4), in a manner analogous to that described, above, for VH dimers. It has been shown (Stevens, 1980, supra) that one amino acid position factors significantly in the natural variation of $K_{LL}$ over a range of at least three orders of magnitude in afinity, resulting in either VLs that have little significant self-association tendency or VLs that dimerize very strongly. For recombinant production of functional Fv assemblies, it is clear that VLs with little self-association tendency are preferred in order to maximize the concentration of free VL available for interaction with VH.

It has been determined that the interactions between VH domain and VL domain amino acids, in a heterologous dimer, occur at the same positions as are found in a homologous VL dimer; in some cases the corresponding VH amino acids are identical. Therefore, examination of VL-VL interactions is an appropriate simulation of VH-VH interactions and a valid approach for identification of structural features by which to control the relative magnitudes of productive heterologous VH-VL associations and non-productive homologous VH-VH and VL-VL associations.

The VL domain interactions are malleable in both affinity and geometry; i.e. relative orientation of domains, and the alterations in interaction properties can be effected by alterations of amino acids that do not contact the antigen. Because of the homology of VL-VL and VH-VH interactions, it is evident that similar properties can be expected to prevail in VH-VH dimers, which have been less extensively studied to date. Therefore, rational substitutions of interfacial amino acids can provide VH and VL domains having diminished homologous interaction tendencies and enhanced heterologous affinity, properties that should significantly increase FAB or Fv production, particularly through recombinant bacterial methodologies.

Figure 2:
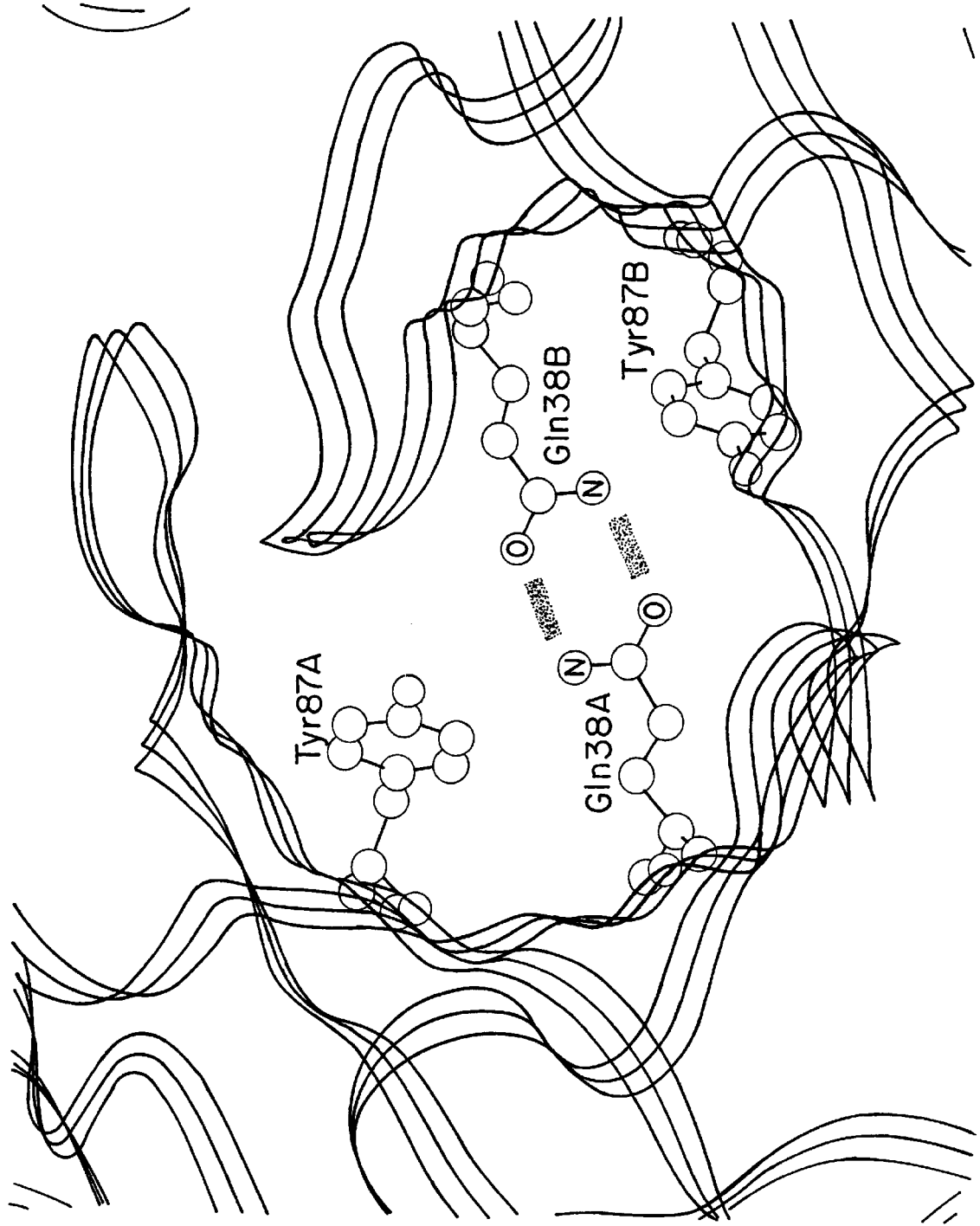
FIG. 2 is a schematic representation of part of the interface of an antibody light chain dimer. Rectangular shaded areas represent two hydrogen bonds between glutamine side chains located at position 38 in the two light chain subunits (designated Gln 38A and Gin 38B, respectively). An identical interaction is found in the interaction between heavy and light chain variable domains in functional Fab and Fv assemblies.

Examination of crystailographically determined three dimensional structures of light chain dimers revealed several positions that contribute to energetically favorable contacts across the VL-VL interface. These positions include residues 36, 38, 87, 89, and 98. The interfacial contact at position 38 is shown schematically in FIG. 2.

By way of illustrating the present invention, reference is made to position 38, in which two hydrogen bonds are generated between two glumine side chains, which are present in nearly all light chains. In heavy chains, a glutamine residue at position 39 plays the same role. Because of the necessity of VL to interact with VH physiologically, these glutamine residues, in both heavy and light chains, are virtually invariant in naturally occurring antibodies. Mutations altering the glutamine on either a heavy or light chain gene would have to be compensated for by a simultaneous mutation on the other gene. Simultaneous compensatory double mutations are extremely unlikely; very few natural occurrences have been observed. However, methods well-known to those skilled in the art can be employed such that it can be accomplished readily in the laboratory.

Without theoretical or empirical constraint, the method of this invention can, in part, be understood by reference to well-known physical principles: like charges repel and opposite charges attract. Naturally occurring positive charges are provided by the basic amino acids such as arginine and lysine; negative charges are imparted by residues such as by glutamic acid and aspartic acid. The proximity of one basic amino acid and one acidic amino acid creates a "salt bridge" which energetically favors strong interaction. Proximity of two acidic or two basic amino acids opposes productive interaction.

For example, if position 38 in a light chain is changed by site-specific mutation from the natural glutamine residue to a lysine, the method of the present invention contemplates that the self-association properties of the VL will be changed significantly. A lysine side chain is one bond longer than the glutamine residue and therefore would occupy too much volume in the domain—domain interspace. Moreover, a lysine side chain would be positively charged; formation of the standard dimer would require bringing two positive charges into close proximity, which could only be accomplished at the expense of a large amount of free energy. Dimerization constants for VL-VL interaction range from approximate $10^4$ $M^{-1}$ to $10^7$ $M^{-1}$. These aimlities represent free energy changes of approximately 6 to 11 kcal $mol^{-1}$. Loss of the two hydrogen bonds formed by the two glutamine side changes would reduce the maximum free energy available from dimerization to approximately 7 kcal $mol^{-1}$ corresponding to a equilibrium constant between $10^4$ to $10^5$ $M^{-1}$. A conservative estimate of the energy required to force the two lysines into proximity is 4 kcal $mol^{-1}$. Therefore, the maximum free energy change that would occur for the interaction of two light chains with lysine at position 38 would be on the order of 3 kcal $mol^{-1}$ generating a dimerization constant of $10^2$ M$^{-1}$, which corresponds to effectively no dimerization at meaningfuil protein concentrations.

Therefore, by way of illustrating this invention, replacement of glutamine 38 by lysine would dramatically alter the dimerization properties of the VL. Similar considerations guide the various embodiments of this invention. An argument can be made against replacement of glutamine by arginine, which—like lysine—has a long, positively charged side chain. Glutamic acid is a negatively charged amino acid whose side chain is the same size found for glutamine; therefore, this substitution would not block dimerization through volumetric considerations but substantial decrease in dimerzation tendency would result from the attempt to bring two negative charges into relatively close proximity. Aspartic acid is also a negatively charged residue; decreased dimerization is expected through loss of hydrogen bonding although charge repulsion effects will be less dramatic than found with the other proposed amino acid replacements. Replacement of glutamine 39 by such charged amino acids in VH would result in parallel reduction of dimerization properties of VH. However, because VH domains typically have two strongly hydrophobic tryptophan residues on their respective interfaces, a replacement of glutamine 39 alone may not be sufficient to totally eliminate VH dimerization. The method of this invention, therefore, also contemplates modification and/or removal of one or both tryptophan residues in order to diiminisih the self-association tendency of this subunit.

Figure 3:
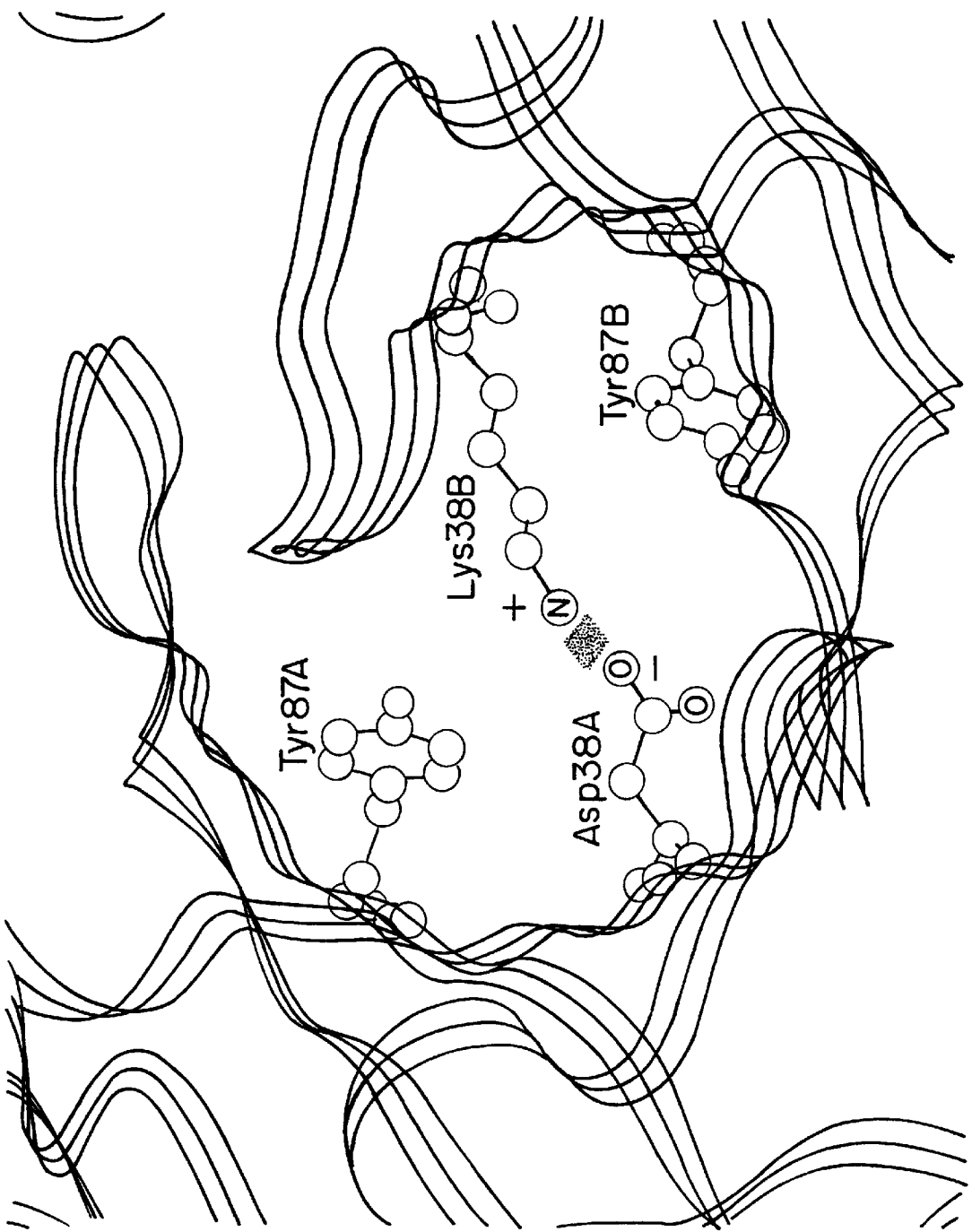
FIG. 3 is a schematic representation of an interaction between antibody light chains in which glute at position 38 is replaced by the negatively charged aspartic acid in one chain, and by the positively charged amino acid, lysine, in the other. Because close proximity of opposite charges is energetically favorable, but proximity of identical charges is energetically unfavorable, these or analogous substitutions will minimize homologous dimer formation and maximize heterologous dimer formation.

Referring to FIG. 3, a schematic representation of a light chain interaction of the type consistent with the present invention, aspartic acid can be substituted at position 38. Because aspartic acid is shorter than glutamine, space exists to accommodate the extra atoms introduced by substitution of lysine or arginine for glutamine in another light chain. Because aspartic acid is negatively charged, whereas lysine and arginine side chains are positively charged, proximity of aspartic acid to either lysine or arginine is energetically favorable. VLs with aspartic acid at position 38 will have little ability to self-associate; VHs with lysine or arginine at position 39 will have strongly diminished self-association capacity. A mixture of such modified VLs and VHs will have a strong tendency to form heterologous dimers; i.e., functional Fabs or Fvs.

The strategies underlying the present invention are applicable to the genes of antibodies after the antibody has been identified. If introduction of an interface substitution affects the specificity, affinity or dynamics of the antibody-antigen interaction, compensatory measures include, without limitation, introduction of alternative residues at critical interface positions, such that alteration of the hydrogen-bonding patterns or side-chain volume induces an adjustment of the VH-VL relative positions. Compensation of domain—domain interactions to restore original functionality is avoidable through use of phage-display or other similar techniques which bypass the need to immunize animals to screen libraries of VH and VL genes, in which amino acid substitutions have been incorporated prior to antibody selection.

The following non-limiting examples illustrate these and other features of the invention.

EXAMPLES OF THE INVENTION

In the examples which follow, the variant human kappa-IV light chains of this invention, modified at position 38, were interacted one with another to demonstrate productive heterologous dimerization/Fv formation. As described more fully below, the variant kappa-IV light chains were obtained from the expression of the corresponding nucleic acid sequences (SEQ ID NOS: 1, 3 and 5), via recombinant technology. The variants substituted arginine (R), aspartic acid (D), or lysine (K) for glutamine at position 38 (adopting, for purposes of these examples, the single letter expression rule confirmed by IUPAC-IUB chemistry nomenclature).

The results summarized in each of the following examples were obtained using size-exclusion chromatography, which includes various methods well-known to those skilled in the art and well-suited to demonstrate the efficacy of the inventive method. Size-exclusion chromatography partitions moecules and molecular complexes on the basis of their Stokes radii or hydrodynamic volumes. As a result, the chromatographic properties of a mixture of interacting macromolecules generate an elution profile that differs from a synthetic profile constructed by suainmtion of elution profiles exhibited by the molecules chromatographed separately. In conjunction with gel filtration technology, size-exclusion chromatography can be used for quantitative protein-ligand interaction analyses and to demonstrate protein-protein interactions. In each of the following examples, increased dimeriztion is reflected as an increased average molecular weight of the molecular components and earlier elution Dilution of the sample, therefore, leads to later elution.

More specifically with respect to Examples 1–4, the HPLC system used to obtain the given results consisted of a 0.3-cm×25-cm glass column (Alltech Associates) packed with Superose 12 (Pharmacia) and a Pharmacia 2248 HPLC pump at a flow rate of 0.06 ml/min. The mobile phase consisted of 20 mM potassium phosphate, 100 mM NaCl, pH 7.0. All experiments were performed at room temperature. The variant proteins were characterized and eluted, with their profiles plotted ( ), using the following concentrations: In Example 1 (FIG. 4), Q38D ( - - - ) 20.0 mg/ml, Q38R ( . . . ) 20.0 mg/ml, and Q38D+R (____) 10.0 mg/ml each of Q38R and Q38D; In Example 2 (FIG. 5), Q38D ( - - - ) 10.0 mg/ml, Q38R ( . . . ) 10.0 mg/ml, and Q38D+R (____) 5.0 mg/ml each of Q38D and Q38R; In Example 3 (FIG. 6), Q38D ( - - - ) 2.0 mg/ml, Q38R ( . . . ) 2.0 mg/ml, and Q38D+R (____) 1.0 mg/ml each of Q38D and Q38R; In Example 4 (FIG. 7), Q38D ( - - - ) 2.0 mg/ml, Q38K ( . . . ) 2.0 mg/ml, and Q38D+K (____) 1.0 mg/ml each of Q38D and Q38K. The protein samples were injected in a volume of 5 μl with a Rheodyne 7010 injection valve. The column eluent was monitored at 214, 280, or 254 in by an HP 1040λ diode array detector. Typical run times ranged from 30 to 45 min. The data were collected and stored according to procedures well-known in the art. Chromatograms were normalized by surmmnation of the absorbances at 1000 data points collected during the run and by scaling the data so that the integrated area under each elution profile was equal to 1. This allowed evaluation of differences in protein aggregation uncomplicated by peak-height differences due to varying amounts of protein applied.

Examples 1–3

Figure 4:
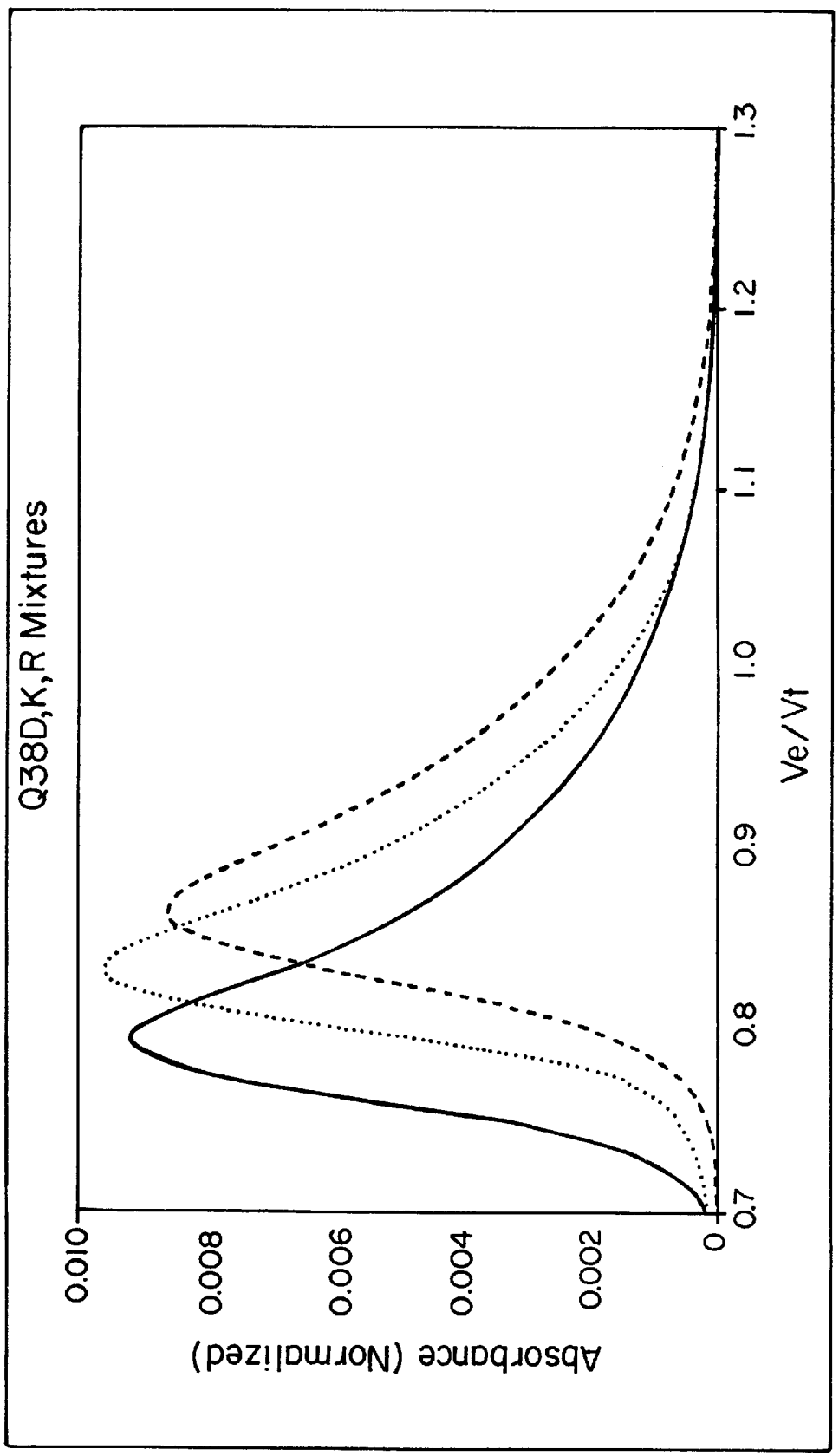
FIGS. 4–7 graphically show the elution characteristics of the recombinant position 38 -modified human kappa-IV light chains of the present invention: Q38D (aspartic acid variant), Q38R (arginine variant) and Q38D&R (mixture of D and R variants) in FIGS. 4–6; and Q38D (asparic acid variant), Q38K (1 lysine variant) and Q38D&K (mixture of aspartic acid and lysine variants) in FIG. 7—using IUPAC-IUB Biochemistry Nomenclature to designate the position 38 variants and the substituted amino acid residues.
Figure 5:
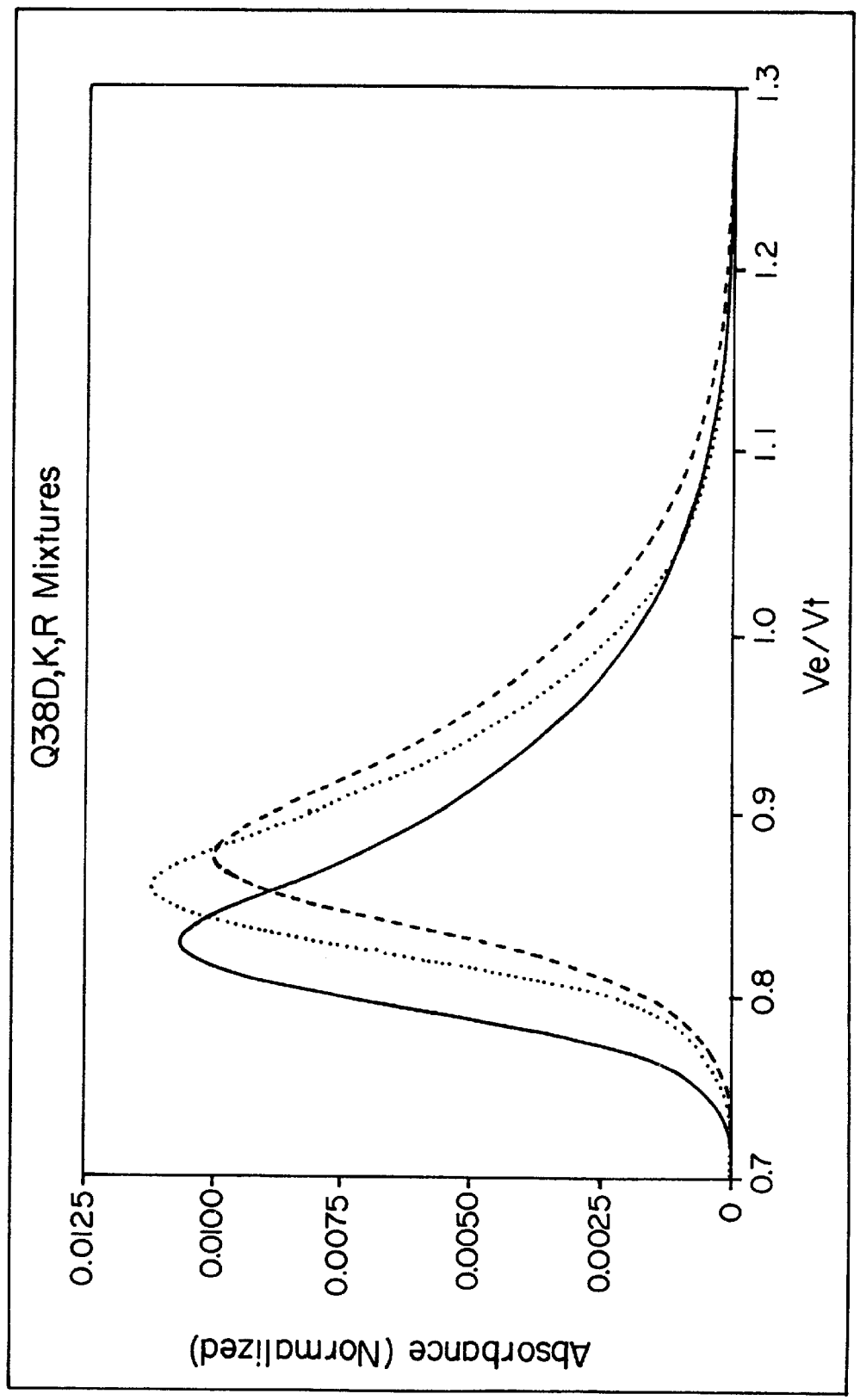
Figure 6:
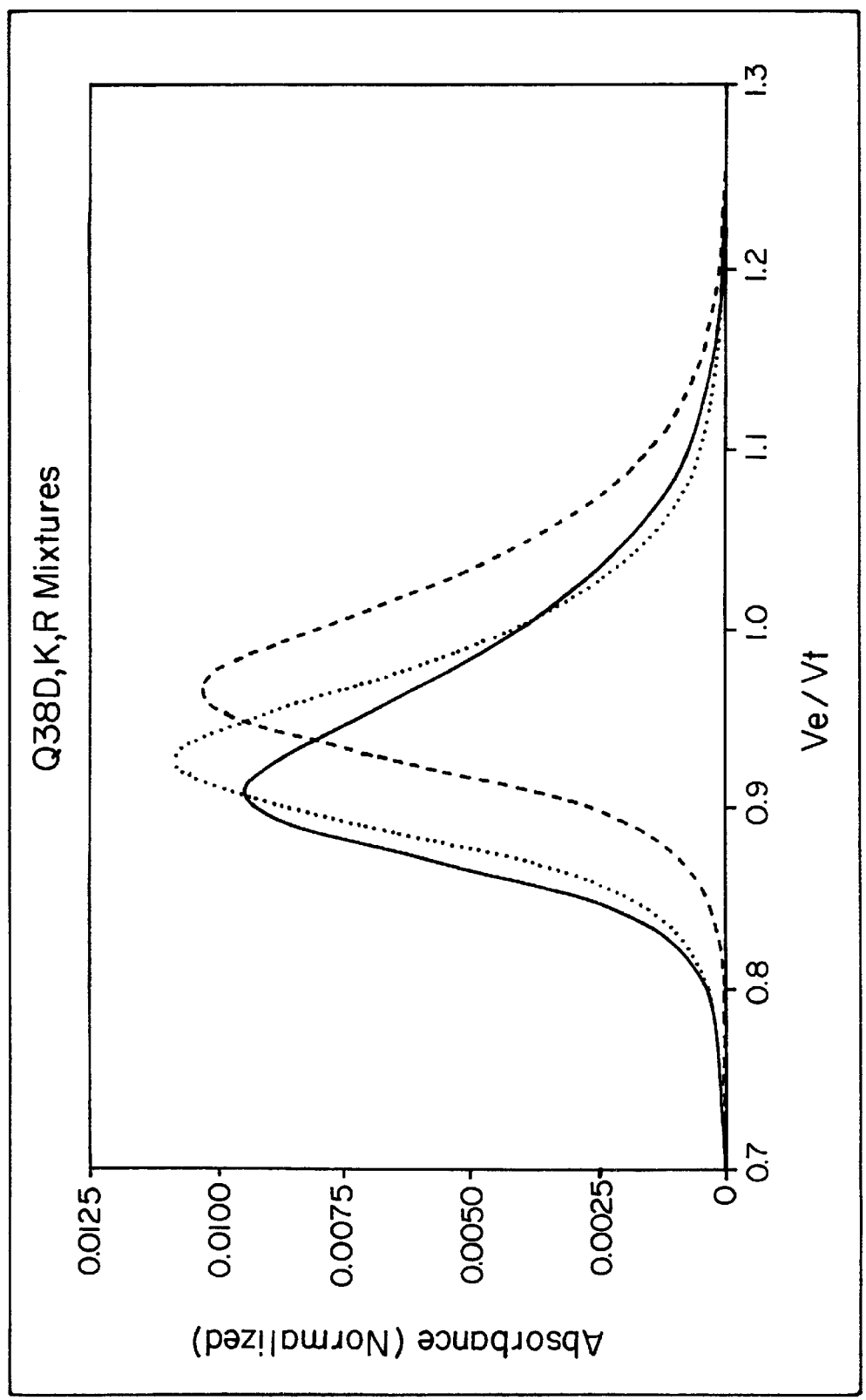

With reference to FIGS. 4–6, respectively, the interaction of the arginine (R) and aspartic acid (D) variants shows most dramatically the utility of the inventive methods, provides dramatic evidence of promoting favored heterologous dimerizations, and demonstrates the utility of such light chains as part of a panel to characterize fibril formation. At all concentrations evaluated, the mixture of D and R variants eluted earlier than monomeric samples of either D or R, at the same total concentration.

Example 4

Figure 7:
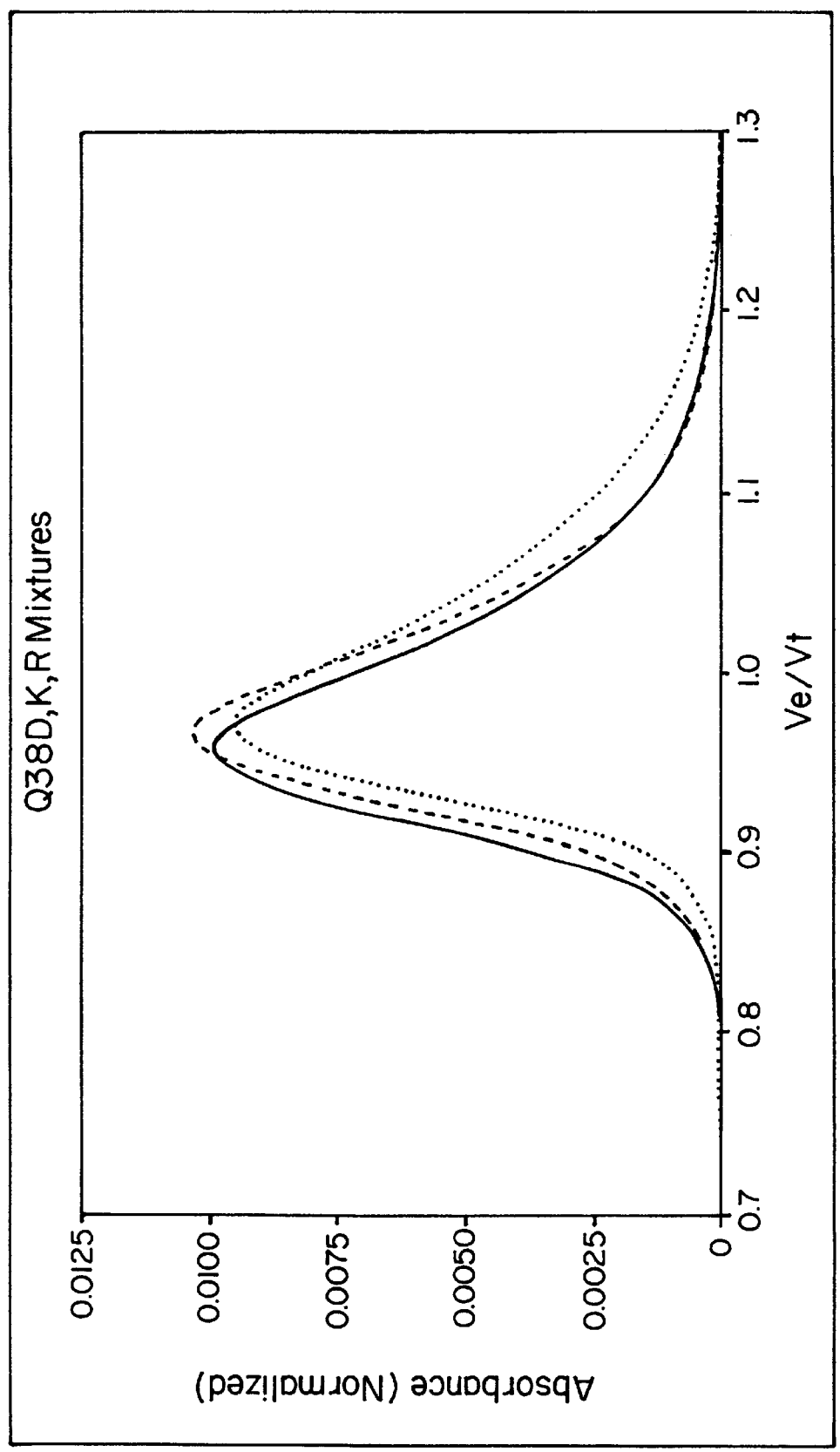

With reference to FIG. 7, aspartic acid (D) and lysine (K) variants of the present invention were interacted one with the other, then analyzed in a manner analogous to that described above. At the concentration shown, a mixture of D and K—heterologous dimerization—eluted earlier than the monomeric samples of either D or K, at the same total concentration.

Example 5

Preparation and Isolation of the Nucleic Acid Sequence Encoding for Each Variant Kappa-4 Light Chain A. Origin of pkIVlen004 Template Plasmid.

The template nucleic acid sequence from which the variant kappa-4 light chains were constructed was pkIVlen004, a plasmid which encodes the V-domain sequence of the human kappa-4 light chain Len. The amino acid sequence of light chain Len was published in 1974 (See Schneider and Hilschmann, The Primary Structure of a Monoclonal Immunoglobulin L-chain of κ-type, subgroup IV (Bence-Jones protein Len): A New Subgroup of the κ-type L-chain. *Hoppe-Seyler's Z. Physiol. Chem.* 355:1164–1168, 1974). More recently, the protein was resequenced, and amino acids at all positions were confirmed with the exception of position 9, where an Asp was found instead of the Asn previously reported.

The Len sequence contains a single amino acid difference from the germline-encoded sequence of the human kappa-4 V-region exon (Klobeck et al, Subgroup IV of Human Immunoglobulin κLight Chains is Encoded by a Single Germline Gene. *Nucl. Acids Res.* 13:6515–6529, 1985): a substitution of Ser for Asn at position 29. A synthetic gene encoding the Len sequence was constructed starting from the human V-kappa4 germline exon, which is available from American Tissue Culture Collection (Rockville, Md., clone #61121). The BamHI-SphI fragment containing the V-kappa-4 exon was subcloned into the bifunctional vector pBS+/− (Stratagene, La Jolla, Calif.) and amplified by polymerase chain reaction (PCR) techniques (See Saiki et al., Enzymatic Amplification of β-Globin Genomic Sequences and Restriction Site Analysis for Diagnosis of Sickle Cell Anemia. *Science* 230:1350–1354, 1985) with a sense-strand primer which positioned a HincII site at the first codon of the mature light chain (Asp 1) and an antisense-strand primer which added to the 3' end of the V-region exon the 12 codons of the LEN J-segment (Tyr96-Lys107), tandem stop codons, and a HindIII site. The amplified fragment was digested with HincII and HindIII and cloned into the vector pASK40 (See, Skerra et al., The Functional Expression of Antibody Fv fragments in *Escherichia coli*: Improved Vectors and a generally applicable Purification Technique. *Bio/Technology* 9:273–278, 1991) which had been digested with EcoRI, blunted with mung bean nuclease, and digested with HindIII. This generated a complete germline-type V-kappa-4 domain coding region following the ompA signal sequence of the pASK40 vector, with an additional Ala codon encoded at the junction of the blunted EcoRI site of the vector with the HincII site of the insert. By site-specific mutagenesis (Kunkel et al., Rapid and Efficient Site-Specific Mutagenesis without Phenotypic Selection. *Meth. in Enzymol.* 154:367–382,1987), the codon for Asn29 was mutated to Ser to generate the Len coding region. By recombinant PCR (See Higuchi et al., A General Method of in vitro Preparation and Specific Mutagenesis of DNA Fragments: Study of Protein and DNA interactions. *Nucl. Acids Res.* 16:7351–7367, 1988), the additional Ala codon at the beginning of the Len constaut was removed, and a codon for a terminal Arg (Arg 108) was added at the 3' end of the construct. The pASK40-based plasmid containing the Len V-kappa-4 domain coding sequence, designated pkIVlen004, served as template for the Q38 mutants described below.

B. Constructon of Plasmids Encoding Q38D, 038R, and Q38K Variants.

To generate the Q38 variant nucleic acid sequences of the present invention, the pkIVen004 plasmid described above was used as template for recombinant PCT (See Higuchi et al., supra). In the first PCR round, two overlapping fragments of approximately 240 base pairs each were generated:

1. a 5' fragment from the XbaI site to the region containing the Q38 variant codon. Each 5' fragment was generated from sense-strand primer K4PRIMER_1S (SEQ ID NO: 8) (or MINUS35_1S (SEQ ID NO:7), in the case of the Q38K mutant) and an antisense-strand primer specific for the variant being generated, K4LEN_Q38D_A (SEQ ID NO: 12), K4LEN_Q38R_A (SEQ ID NO: 13), or K4LEN_Q38K_A (SEQ ID NO: 14) for Q38D, Q38R, and Q38K variants, respectively.

2. a 3' fragment from the region containing the Q38 variant codon to the HindIII site. Each 3' fragment was generated from antisense-strand primer LEN_TERM_R (SEQ ID NO: 15) and a sense-strand primer specific for the variant being generated, K4LEN_Q38D_S (SEQ ID NO: 9), K4LEN_Q38R_S (SEQ ID NO: 10), or K4LEN_Q38K_S (SEQ ID NO: 11) for Q38D, Q38R, and Q38K variants, respectively.

In a second round of PCR, each pair of two overlapping fragments from the first PCR round was combined and amplified with sense-strand primer K4PRIMER_1S (SEQ ID NO: 8) (or MINUS35_1S (SEQ ID NO: 7), in the case of the Q38K mutant) and antisense-strand primer LEN_TERM_R (SEQ ID NO: 15) to generate a fragment of about 450 base pairs (or about 540, in the case of the Q38K mutant). These fragments were digested with XbaI and HindIII and inserted into XbaI/HindIII-digested pASK40 vector. Sequences of primers used in constructing these clones are listed in Table 1, below.

TABLE 1

Sequences of oligos used to construct Q38D, Q38R, and Q38K nucleic acid sequences from pkIVlen004 template plasmid (SEQ ID NOS: 7–15)

| | |
|---|---|
| MINUS35_1S | GGCTTTACAC TTTATGCTTC CG |
| K4PRIMER_1S | AGAGGAGGCA TGATTACGAA TTTCTAGATACGAGGG |
| K4LEN_Q38D_S | GGTATCAGGA CAAACCAGGA CAGCCTCC |
| K4LEN_Q38R_S | GGTATCAGCG TAAACCAGGA CAGCCTCC |
| K4LEN_Q38K_S | GGTATCAGAA GAAACCAGGA CAGCCTCC |
| K4LEN_Q38D_A | GGTTTGTCCT GATACCAAGC TAAGTAGTTCTTAGAGTTGG |
| K4LEN_Q38R_A | GGTTTACGCT GATACCAAGC TAAGTAGTTCTTAGAGTTGG |
| K4LEN_Q38K_A | GGTTTCTTCT GATACCAAGC TAAGTAGTTCTTAGAGTTGG |
| LEN_TERM R | CACAGGTCAA GCTTAGCGTT TGATTTCCAG |

Two codons were altered by each of the specific Q38 primners: the codon for Tyr 36 was changed from TAC to TAT, which deletes a KpnI site from clones containing the mutant Q38 sequences; and the CAG codon for Q38 was changed to GAC, CGT, or AAG to encode an Asp, Arg, or Lys residue, for the Q38D, Q38R, and Q38K variants, respectively. See SEQ ID NOS: 1, 3 and 5 and FIG. 8 (SEQ ID NOS: 2, 4 and 6).

Clones were screened by digesting mini-prep DNAs from the clones with XbaI and KpnI; clones which had incorporated a variant Q38 sequence release a single 0.4 kb insert ent in this digest Using the same two enzymes, the template plasmid, pkIVlen004, releases two faaents of about 0.2 kb, since the KpnI site which contains the codon for Tyr 36 is intact Potential clones were sequenced throughout the entire light chain variabledomm. coding region to verify that the desired mutation had been incorporated properly and that no other mutations had been intoduced during the PCR process.

Example 6

Origin, Source, and Designation or Host Organisms

Plasmids containing sequences encoding the Q38D, Q38R, and Q38K variants of the Len kappa-4 variable regions (See, SEQ ID NOS: 1, 3 and 5, respectively) were maintained in *E. coli* host strain DH5α ([F-80dlacZΔM15 ΔlacZYA-argF)U169 endA1 recA1 hsdR17($r_K$-$M_K$+) deoR thi-1 supE44 1$^-$gyrA96 relA1], Gibco-BR1 Life Technologies, Inc. Gaithersburg, Md.). For expression of the variant kappa-4 sequences, *E. coli* host strain BL26 ([F$^-$, ompT $r_B$-$m_B$-lac) Novagen, Madison, Wis.) was used, as it lacks both the ompT outer membrane protease and the lon cytoplasmic protease.

Example 7

Preparation of Transformants and Use of Cloning Vectors

Frozen competent cells were prepared from *E. coli* host strains using the calcium chloride method, essentially as described in Sambrook et al., *Molecular Cloning: A Laboratory Manual*, 2nd ed.; Cold Spring Harbor, N.Y.; Cold Spring Harbor Laboratory Press, 1989. Competent cells were transformed by incubating 30 minutes on ice an aliquot of the thawed cells mixed with about 0.5–5 ng plasmid DNA, transferring the cell mixture to 37° C. for 1 minute, and returing the mixture to ice for 2 minutes prior to plating the cell mixture on agar plates containing a selective antibiotic (ampicillin or carbenicillin was used for pASK40-based plasmids). Transformants which contain plasmid are antibiotic resistant and form colonies on the selective agar plates, while cells without plasmid do not survive.

Construction of the cloning and expression vector pASK40 was as described in Skerra et al., supra, 1991, and was the kind gift of Dr. Arne Skerra (Max-Planck-Institut fur Biochemie, Martinsried, FRG). The vector pASK40 positions a coding region for the ompA leader sequence prior to the polylinker so that the recombinant proteins produced are directed to the periplasmic space. The oxidizing environment of this compartmenet facilitates correct folding and disulfide-bond formation within the recombinant protein (See Skerra et al., supra 1991).

Example 8

Cultivation of Transformants

Host strain DH5α transformed with plasmid encoding one of the Q38 variants of the Len kappa-4 variable region was grown at 37° C. in 2XYT media (Sambrook et al., supra 1989) containing either 100 μml ampicillin or 100 μg/ml carbenicillin as the selective antibiotic.

For synthesis of the recombinant variant proteins, host strain BL26 transformed with plasmid encoding one of the Q38 variants of the Len kappa-4 variable region was grown at 30° C. in 2XYT media (Sambrook et al., 1989) containing 100 μg/ml carbenicillin as the selective antibiotic.

Example 9

Isolation, Purification, and Yield of Expressed Variants

Cultures of BL26 cells transformed with plasmids encoding Q38 variant proteins were grown to an $A_{595}$ of 0.75 to 1.0, and expression was induced by addition of isopropyl β-D-thiogalactopyranoside (IPTG) to a final concentration of 1 mM. Cell growth was continued for an additional 16 hr. A low agitation rate (100–115 rpm) and 30° C. temperature were used throughout the growth period to avoid cell lysis.

Preparation of periplasmic extracts was based on the method of Pluckthun and Knowles, The Consequences of Stepwise Deletions from the Signal-Processing Site of β-lactase. *J. Biol. Chem.* 262:3951–3957, 1987. Cells were harvested by centrifugation at 4000×g for 10 min. at 4 C. The cell pellet from each liter of culture was gently resuspended in 20 ml ice cold TES buffer (200 mM Tris, 0.5 mM EDTA and 0.5 M sucrose, pH 8.0). One ml of a freshly prepared solution of lysozyme (20 mg/ml in TES) was added to the suspension, followed by 40 ml TES diluted 1:1 in water. The cells were incubated on ice for one hour with gentle shaking and then centrifuged at 27,000×g for 15 min at 4° C., with the supernatant constituting the periplasmic fraction.

The periplasmic fraction from 2 liters starting culture was dialyzed against 10 mM Tris, pH 8.0. The volume was reduced by ultrafiltration on an Amicon stirred cell (YM3 membrane), and the sample was applied at a flow rate of 0.7 ml/min to two 5 ml Macroprep Q cartridges (Bio-Rad, Hercules, Calif.) connected in series and equilibrated with the same Tris buffer. Recombinant Q38 variant proteins were cluted in the flow-through fraction. Fractions containing recombinant proteins were identified by SDS-PAGE analysis, exchanged into 10 mM NaOAc, pH 5.6, by ultrafiltration, and applied at 0.7 ml/min to two 5 ml Macroprep S cartridges (Bio-Rad, Hercules, Calif.) connected in series and equilibrated with the same acetate buffer. The recombinant Q38 variant proteins were eluted from the S-cartridge with a 135 ml 0–150 mM NaCl gradient. Fractions contaning recombinant proteins were exchanged into 20 mM TrisCl, 150 mM NaCl, pH 7.2, concentrated by ultrafiltration, and applied at a flow rate of 0.5 ml/min to a HiLoad 16/60 Superdex 75 gel filtration column (Pharmacia, Piscataway, N.J.) equilibrated with the same buffer. Purified recombinant proteins were exchanged into HPLC buffer (20 mM potassium phosphate, 100 mM NaCl, pH 7.0), concentrated by ultrafiltaion to 30–50 mg/mL and stored at 4° C.

Typical yields for the recombinant proteins were 1.2, 3.5, and 1.9 mg/liter starting culture for the Q38D, Q38R, and Q383 variants, respectively.

Example 10

Confirmation and/or Characterization of Peptide Structure with Desired Amino Acid Substitutions That the recombinant Q38D, Q38R, and Q38K proteins fold into the correct conformation is demonstrated by the fact that in HPLC analysis recombinant variant kappa-4 light chain proteins migrate at an appropriate position for light chain V-kappa monomers and associate to form V-kappa dimers which migrate at the appropriate position.

While the principles of this invention have been described in connection with specific embodiments, it should be understood clearly that these descriptions are made only by way of example and are not intended to limit the scope of the invention, in any manner. For example, while certain amino acid substitutions have been shown and/or disclosed, a broader consideration is coordinated and/or simultaneous introduction of functionally complementary changes to both portions of the antibody subunits which are otherwise highly-conserved. In such a way, the present invention facilitates the use of bacteria, rather than animals, as a source of antibodies. As a means for quality control of antibodies and antibody-based products, the present invention can be used in conjunction with other well-known techniques for the purpose of developing genetically engineered. antibodies and optimizing their performance. For instance, this invention contemplates a flier increase in yield by expressing the VH gene alone in one recombinant bacteria and the VL gene alone in a second recombinant bacteria, followed by in vitro purification of the individual subunits.

This invention is not limited, in any manner, by any commercial, experimental, or theoretical implication of the present methods. Increased antibody production and purity, such as that available through the use of the present invention, is crucial to the imnmunodiagnostics industry. Likewise, the principles of the present invention can be extended to the use of antibodies for immunotherapy: to the extent that diminished efficacy of immunotherapy treatment is related to non-optimal VL-VH interactions, the methods of this invention can be extended to overcome such deficiencies and increase treatment benefits. Other applications of the present invention include those which utilize molecular reagents that recognize and specifically bind other molecules at low concentrations. In agriculture, such applications include veterinary immunodiagnostics, as well as related tests/determinations to evaluate potential bacterial, fungal, or chemical contamination of meats, grains, and other commodities. Environmentally, the present invention is applicable for use in evaluation of remediation sites and, with the increased yields available through use of the present methods, such antibodies can be used to remove contaminants at low concentrations. Industrially, antibodies produced in conjunction with the present method could be used as interfaces for molecularly-specific process monitors, and in such a manner improve productivity through exacting control of reaction conditions.

Other advantages and features of the invention will become apparent from the claims, sequences and figures hereinafter, with the scope of the claims determined by the reasonable equivalents as understood by those skilled in the art.

What is claimed is:

1. A method for altering antibody light chain polypeptide interactions, comprising:

providing a first nucleic acid sequence which codes for an immunoglobulin antibody kappa-IV light chain polypeptide, wherein the codon of the first nucleic acid which codes for position 38 of the immnunoglobulin antibody kappa-IV light chain polypeptide, numbered according to the Wu-Kabat convention, has been modified to code for a first charged amino acid selected from the group consisting of aspartic acid, glutamic acid, arginine, and lysine;

expressing said first nucleic acid sequence to produce modified immunoglobulin antibody kappa-IV light chain polypeptides; and interacting said modified inmnunoglobulin antibody kappa-IV light chain polypeptides with each other.

2. The method as defined in claim 1, wherein said first nucleic acid sequence is selected from the group consisting of the sequences shown in SEQ ID NO: 1, SEQ ID NO: 3 and SEQ ID NO: 5.

3. A method for modulating the affinity between immunoglobulin light chain polypeptides, comprising:

providing a plurality of first light chain kappa-IV Len polypeptides that have a first charged amino acid selected from the group consisting of aspartic acid, glutamic acid, arginine, and lysine at position 38, numbered according to the Wu-Kabat convention, of the polypeptides; and interacting said first light chain kappa-IV Len polypeptides with each other.

4. The method as defined in claim 3, wherein said first polypeptide is encoded by a first nucleic acid sequence selected from the group consisting of the sequences shown in SEQ ID NO: 1, SEQ ID NO: 3 and SEQ ID NO: 5.

5. The method of claim 1 further comprising measuring the interaction of said modified immunoglobulin antibody kappa-IV light chain polypeptides.

6. The method of claim 1 wherein said first nucleic acid sequence has a codon which codes for aspartic acid at position 38 of the immunoglobulin antibody kappa-IV light chain polypeptide.

7. The method of claim 1 wherein said first nucleic acid sequence has a codon which codes for glutamic acid at position 38 of the immunoglobulin antibody kappa-IV light chain polypeptide.

8. The method of claim 1 wherein said first nucleic acid sequence has a codon which codes for arginine at position 38 of the immunoglobulin antibody kappa-IV light chain polypeptide.

9. The method of claim 1 wherein said first nucleic acid sequence has a codon which codes for lysine at position 38 of the immunoglobulin antibody kappa-IV light chain polypeptide.

10. The method of claim 8 further comprising:

providing a second nucleic acid sequence which codes for an immunoglobulin antibody kappa-IV light chain polypeptide, wherein the codon of the second nucleic acid which codes for position 38 of inmmunoglobulin antibody kappa-IV light chain polypeptide has been modified to code for aspartic acid;

expressing said second nucleic acid sequence to produce different modified immunoglobulin antibody kappa-IV light chain polypeptides; and interacting said modified immunoglobulin antibody kappa-IV light chain polypeptides with said different modified immunoglobulin antibody kappa-IV light chain polypeptides.

11. The method of claim 10 further comprising measuring the interaction of said modified immunoglobulin antibody kappa-IV light chain polypeptides and said different modified immunoglobulin antibody kappa-IV light chain polypeptides.

12. The method of claim 1 wherein the modified immunoglobulin antibody kappa-IV light chain polypeptides are immunoglobulin antibody human kappa-IV light chain Len polypeptides.

13. The method of claim 3 further comprising measuring the interaction of said first light chain kappa-IV Len polypeptides.

14. The method of claim 3 wherein the first light chain kappa-IV polypeptides have an aspartic acid at position 38.

15. The method of claim 3 wherein the first light chain kappa-IV polypeptides have a glutamic acid at position 38.

16. The method of claim 3 wherein the first light chain kappa-IV polypeptides have an arginine at position 38.

17. The method of claim 3 wherein the first light chain kappa-IV polypeptides have a lysine at position 38.

18. The method of claim 16 further comprising:

providing a plurality of second light chain kappa-IV Len polypeptides that have an aspartic acid at position 38 of the polypeptides; and interacting said plurality of first light chain kappa-IV Len polypeptides and said plurality of second light chain kappa-IV Len polypeptides.

19. The method of claim 18 further comprising measuring the interaction between said first light chain kappa-IV Len polypeptides and said second light chain kappa-IV Len polypeptides.

* * * * *

UNITED STATES PATENT AND TRADEMARK OFFICE
CERTIFICATE OF CORRECTION

PATENT NO. : 6,485,943 B2
DATED : November 26, 2002
INVENTOR(S) : Fred J. Stevens et al.

It is certified that error appears in the above-identified patent and that said Letters Patent is hereby corrected as shown below:

Column 1,
Line 9, "of, Chicago" is changed to -- of Chicago --.
Lines 20-21, "unmunoglobulin" is changed to -- immunoglobulin --.
Line 26, "unmunoglobulin" is changed to -- immunoglobulin --.
Line 64, "fuil" is changed to -- full --.

Column 2,
Line 6, "leavy" is changed to -- Heavy --.
Line 9, "ChenL" is changed to -- Chem --.
Line 12, "fornation" is changed to -- formation --.
Line 12, "Amvloid" is changed to -- Amyloid --.
Line 48, "θ" is changed to -- λ, --.
Line 67, "fimdalmentally" is changed to -- fundamentally --.

Column 3,
Line 17, "deteimining" is changed to -- determining --.
Line 34, "chais" is changed to -- chains --.
Line 35, "exammation" is changed to -- examination --.
Line 42, "And." is changed to -- Natl. --.
Line 43, "anct-" is changed to -- and --.
Line 44, "immunoglobulii" is changed to -- immunoglobulin -- .
Line 49, "Solubilintion" is changed to -- Solubulization --.
Lines 50-51, "amy-loidladen" is changed to -- amyloid-laden --.

Column 4,
Lines 10-11, "anii-mal" is changed to -- animal --.
Line 16, "maiial" is changed to -- maximal --.
Line 46, "iiveiion" is changed to -- invention --.
Line 51, "fotmation" is changed to -- formation --.
Line 53, "fcragent" is changed to -- fragment --.
Line 55, "suce" is changed to -- such --.
Line 60, "cbncombinantly" is changed to -- concombinantly --.

Column 5,
Line 2, "fragnent" is changed to -- fragment --.
Line 40, "Gin" is changed to -- Gln --.
Line 45, "glute" is changed to -- glutamine --.
Line 57, "aspartic" is changed to -- aspartic --.

UNITED STATES PATENT AND TRADEMARK OFFICE
CERTIFICATE OF CORRECTION

PATENT NO. : 6,485,943 B2
DATED : November 26, 2002
INVENTOR(S) : Fred J. Stevens et al.

It is certified that error appears in the above-identified patent and that said Letters Patent is hereby corrected as shown below:

Column 6,
Line 1, "SEQ ID NOS: 2,4,6,8,10,12 and 14" is deleted.
Lines 1-2, "SEQ ID NOS: 16, 18,20,22,24,26 and 28" is deleted.
Lines 9-11, "43-49, SEQ ID NOS: 30,32,34,36,38,40 and 42, SEQ ID NOS: 2,4,6,8,10, 12 and 14, and SEQ ID NOS: 16,18,20,22,24,26 and 28, respectively" is changed to -- 1,3 and 5 --.

Column 9,
Lines 6, 29, 31 and 33, "→←" is changed to -- ↔ --.
Line 44, "vitally" is changed to -- virtually --.

Column 10,
Line 20, "glumine" is changed to -- glutamine --.
Line 57, "aimlities" is changed to -- affinities --.

Column 11,
Line 2, "meaningfuil" is changed to -- meaningful --.
Line 28, "diiminisih" is changed to -- diminish --.

Column 12,
Line 14, "moecules" is changed to -- molecules --.
Line 18, "suainmtion" is changed to -- summation --.
Line 24, "dimeriztion" is changed to -- dimerization --.
Line 25, "elution Dilution" is changed to -- elution. Dilution --.
Line 51, "surmmnation" is changed to -- summation --.

Column 14,
Line 2, "constaut" is changed to -- construct --.
Line 12, "PCT" is changed to -- PCR --.
Line 63, "primners" is changed to -- primers --.

Column 15,
Line 6, "ent" is changed to -- fragment --..
Line 6, "digest Using" is changed to -- digest. Using --.
Line 9, "intact Potential" is changed to -- intact. Potential --.
Line 10, "variabledomm." is changed to -- variable domain --.
Line 53, "compartmenet" is changed to -- compartment --.
Line 63, "µml" is changed to -- µg/ml --.

UNITED STATES PATENT AND TRADEMARK OFFICE
CERTIFICATE OF CORRECTION

PATENT NO. : 6,485,943 B2
DATED : November 26, 2002
INVENTOR(S) : Fred J. Stevens et al.

It is certified that error appears in the above-identified patent and that said Letters Patent is hereby corrected as shown below:

Column 16,
Line 53, "ultrafiltaion" is changed to -- ultrafiltration --.

Column 17,
Line 17, "fiier" is changed to -- further --.
Line 25, "imnmunodiagnostics" is changed to -- immunodiagnostics --.

Column 27,
Lines 18 and 27, "immnunoglobulin" is changed to -- immunoglobulin --.

Signed and Sealed this

Seventeenth Day of August, 2004

JON W. DUDAS
*Acting Director of the United States Patent and Trademark Office*

SEQUENCE LISTING

<160> NUMBER OF SEQ ID NOS: 16

<210> SEQ ID NO 1
<211> LENGTH: 342
<212> TYPE: DNA
<213> ORGANISM: Escherichia coli
<220> FEATURE:
<221> NAME/KEY: CDS
<222> LOCATION: (1)..(342)
<223> OTHER INFORMATION:

<400> SEQUENCE: 1

```
gac atc gtg atg acc cag tct cca gac tcc ctg gct gtg tct ctg ggc        48
Asp Ile Val Met Thr Gln Ser Pro Asp Ser Leu Ala Val Ser Leu Gly
1               5                   10                  15 gag agg gcc acc atc aac tgc aag tcc agc cag agt gtt tta tac agc        96
Glu Arg Ala Thr Ile Asn Cys Lys Ser Ser Gln Ser Val Leu Tyr Ser
                20                  25                  30 tcc aac tct aag aac tac tta gct tgg tat cag aag aaa cca gga cag       144
Ser Asn Ser Lys Asn Tyr Leu Ala Trp Tyr Gln Lys Lys Pro Gly Gln
            35                  40                  45 cct cct aag ctg ctc att tac tgg gca tct acc cgg gaa tcc ggg gtc       192
Pro Pro Lys Leu Leu Ile Tyr Trp Ala Ser Thr Arg Glu Ser Gly Val
        50                  55                  60 cct gac cga ttc agt ggc agc ggg tct ggg aca gat ttc act ctc acc       240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgc cag cag       288
Ile Ser Ser Leu Gln Ala Glu Asp Val Ala Val Tyr Tyr Cys Gln Gln
                85                  90                  95 tac tac tcc acc ccg tac tcc ttc ggt cag ggt acc aaa ctg gaa atc       336
Tyr Tyr Ser Thr Pro Tyr Ser Phe Gly Gln Gly Thr Lys Leu Glu Ile
                100                 105                 110 aaa cgc                                                                342
```

Lys Arg

<210> SEQ ID NO 2
<211> LENGTH: 114
<212> TYPE: PRT
<213> ORGANISM: Escherichia coli

<400> SEQUENCE: 2

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Ser Lys Asn Tyr Leu Ala Trp Tyr Gln Lys Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Ser Phe Gly Gln Gly Thr Lys Leu Glu Ile
            100                 105                 110

Lys Arg
```

<210> SEQ ID NO 3
<211> LENGTH: 343
<212> TYPE: DNA
<213> ORGANISM: Escherichia coli
<220> FEATURE:
<221> NAME/KEY: CDS
<222> LOCATION: (1)..(342)
<223> OTHER INFORMATION:

<400> SEQUENCE: 3

```
gac atc gtg atg acc cag tct cca gac tcc ctg gct gtg tct ctg ggc      48
Asp Ile Val Met Thr Gln Ser Pro Asp Ser Leu Ala Val Ser Leu Gly
 1               5                  10                  15 gag agg gcc acc atc aac tgc aag tcc agc cag agt gtt tta tac agc      96
Glu Arg Ala Thr Ile Asn Cys Lys Ser Ser Gln Ser Val Leu Tyr Ser
            20                  25                  30 tcc aac tct aag aac tac tta gct tgg tat cag gac aaa cca gga cag     144
Ser Asn Ser Lys Asn Tyr Leu Ala Trp Tyr Gln Asp Lys Pro Gly Gln
        35                  40                  45 cct cct aag ctg ctc att tac tgg gca tct acc cgg gaa tcc ggg gtc     192
Pro Pro Lys Leu Leu Ile Tyr Trp Ala Ser Thr Arg Glu Ser Gly Val
    50                  55                  60 cct gac cga ttc agt ggc agc ggg tct ggg aca gat ttc act ctc acc     240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgc cag cag     288
Ile Ser Ser Leu Gln Ala Glu Asp Val Ala Val Tyr Tyr Cys Gln Gln
                85                  90                  95 tac tac tcc acc ccg tac tcc ttc ggt cag ggt acc aaa ctg gaa atc     336
Tyr Tyr Ser Thr Pro Tyr Ser Phe Gly Gln Gly Thr Lys Leu Glu Ile
            100                 105                 110 aaa cgc d                                                           343
Lys Arg
```

<210> SEQ ID NO 4
<211> LENGTH: 114

```
<212> TYPE: PRT
<213> ORGANISM: Escherichia coli

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Lys Asn Tyr Leu Ala Trp Tyr Gln Asp Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Ser Phe Gly Gln Gly Thr Lys Leu Glu Ile
            100                 105                 110

Lys Arg

<210> SEQ ID NO 5
<211> LENGTH: 343
<212> TYPE: DNA
<213> ORGANISM: Escherichia coli
<220> FEATURE:
<221> NAME/KEY: CDS
<222> LOCATION: (1)..(342)
<223> OTHER INFORMATION:

<400> SEQUENCE: 5 gac atc gtg atg acc cag tct cca gac tcc ctg gct gtg tct ctg ggc        48
Asp Ile Val Met Thr Gln Ser Pro Asp Ser Leu Ala Val Ser Leu Gly
1               5                   10                  15 gag agg gcc acc atc aac tgc aag tcc agc cag agt gtt tta tac agc        96
Glu Arg Ala Thr Ile Asn Cys Lys Ser Ser Gln Ser Val Leu Tyr Ser
            20                  25                  30 tcc aac tct aag aac tac tta gct tgg tat cag cgt aaa cca gga cag       144
Ser Asn Ser Lys Asn Tyr Leu Ala Trp Tyr Gln Arg Lys Pro Gly Gln
        35                  40                  45 cct cct aag ctg ctc att tac tgg gca tct acc cgg gaa tcc ggg gtc       192
Pro Pro Lys Leu Leu Ile Tyr Trp Ala Ser Thr Arg Glu Ser Gly Val
50                  55                  60 cct gac cga ttc agt ggc agc ggg tct ggg aca gat ttc act ctc acc       240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgc cag cag       288
Ile Ser Ser Leu Gln Ala Glu Asp Val Ala Val Tyr Tyr Cys Gln Gln
                85                  90                  95 tac tac tcc acc ccg tac tcc ttc ggt cag ggt acc aaa ctg gaa atc       336
Tyr Tyr Ser Thr Pro Tyr Ser Phe Gly Gln Gly Thr Lys Leu Glu Ile
            100                 105                 110 aaa cgc d                                                              343
Lys Arg <210> SEQ ID NO 6
<211> LENGTH: 114
<212> TYPE: PRT
<213> ORGANISM: Escherichia coli

<400> SEQUENCE: 6
```

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Asn Ser Lys Asn Tyr Leu Ala Trp Tyr Gln Arg Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Ser Phe Gly Gln Gly Thr Lys Leu Glu Ile
                100                 105                 110

Lys Arg

<210> SEQ ID NO 7
<211> LENGTH: 22
<212> TYPE: DNA
<213> ORGANISM: Unknown
<220> FEATURE:
<223> OTHER INFORMATION: Primer

<400> SEQUENCE: 7
ggctttacac tttatgcttc cg                                              22

<210> SEQ ID NO 8
<211> LENGTH: 36
<212> TYPE: DNA
<213> ORGANISM: Unknown
<220> FEATURE:
<223> OTHER INFORMATION: Primer

<400> SEQUENCE: 8
agaggaggca tgattacgaa tttctagata cgaggg                               36

<210> SEQ ID NO 9
<211> LENGTH: 28
<212> TYPE: DNA
<213> ORGANISM: Unknown
<220> FEATURE:
<223> OTHER INFORMATION: Primer

<400> SEQUENCE: 9
ggtatcagga caaaccagga cagcctcc                                        28

<210> SEQ ID NO 10
<211> LENGTH: 28
<212> TYPE: DNA
<213> ORGANISM: Unknown
<220> FEATURE:
<223> OTHER INFORMATION: Primer

<400> SEQUENCE: 10
ggtatcagcg taaaccagga cagcctcc                                        28

<210> SEQ ID NO 11
<211> LENGTH: 28
<212> TYPE: DNA
<213> ORGANISM: Unknown
<220> FEATURE:
<223> OTHER INFORMATION: Primer
```

-continued

<400> SEQUENCE: 11
ggtatcagaa gaaaccagga cagcctcc                                          28

<210> SEQ ID NO 12
<211> LENGTH: 40
<212> TYPE: DNA
<213> ORGANISM: Unknown
<220> FEATURE:
<223> OTHER INFORMATION: Primer

<400> SEQUENCE: 12
ggtttgtcct gataccaagc taagtagttc ttagagttgg                             40

<210> SEQ ID NO 13
<211> LENGTH: 40
<212> TYPE: DNA
<213> ORGANISM: Unknown
<220> FEATURE:
<223> OTHER INFORMATION: Primer

<400> SEQUENCE: 13
ggtttacgct gataccaagc taagtagttc ttagagttgg                             40

<210> SEQ ID NO 14
<211> LENGTH: 40
<212> TYPE: DNA
<213> ORGANISM: Unknown
<220> FEATURE:
<223> OTHER INFORMATION: Primer

<400> SEQUENCE: 14
ggtttcttct gataccaagc taagtagttc ttagagttgg                             40

<210> SEQ ID NO 15
<211> LENGTH: 30
<212> TYPE: DNA
<213> ORGANISM: Unknown
<220> FEATURE:
<223> OTHER INFORMATION: Primer

<400> SEQUENCE: 15
cacaggtcaa gcttagcgtt tgatttccag                                        30

<210> SEQ ID NO 16
<211> LENGTH: 113
<212> TYPE: PRT
<213> ORGANISM: Escherichia coli

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

-continued

```
Ile Ser Ser Leu Gln Ala Glu Asp Val Ala Val Tyr Tyr Cys Gln Gln
                85                  90                  95

Tyr Tyr Ser Thr Pro Tyr Ser Phe Gly Gln Gly Thr Lys Leu Glu Ile
            100                 105                 110
Lys
```